United States Patent [19]

Fong

[11] Patent Number: 4,769,432

[45] Date of Patent: * Sep. 6, 1988

[54] WATER-SOLUBLE QUATERNARY CATIONIC MONOMERS

[75] Inventor: Dodd W. Fong, Naperville, Ill.

[73] Assignee: Nalco Chemical Company, Naperville, Ill.

[*] Notice: The portion of the term of this patent subsequent to Mar. 29, 2005 has been disclaimed.

[21] Appl. No.: 937,249

[22] Filed: Dec. 3, 1986

Related U.S. Application Data

[62] Division of Ser. No. 621,339, Jun. 15, 1984, Pat. No. 4,659,828.

[51] Int. Cl.$^4$ .................... C08F 14/14; C08F 114/14
[52] U.S. Cl. .................................. 526/291; 526/261; 525/326.7
[58] Field of Search .............................. 526/263, 291; 525/326.7

[56] References Cited

U.S. PATENT DOCUMENTS 2,843,573  7/1958  Melamed .............................. 526/291

OTHER PUBLICATIONS

79 CA 151603f German Offen. 2,312,708 Miyazako, et al.
80 CA 151111g Japanese Kokai 73/85222 Miyazako, et al.
85 CA 51750g German Offen. 2,546,241 Ferruti, et al.
85 CA 51751h German Offen. 2,546,240 Ferruti, et al.
87 CA 85501h German Offen. 2,550,547 Naarmann, et al.
88 CA 89716a German Offen. 2,623,838 Pohlemann, et al.
94 CA 90348n U.S. Pat. No. 4,228,152 Ferruti, et al.
88 CA 113310m Japanese Kokai 77/102722 Chujo, et al.

Primary Examiner—John Kight
Assistant Examiner—M. L. Moore
Attorney, Agent, or Firm—John G. Premo; Anthony L. Cupoli; Donald G. Epple

[57] ABSTRACT

The methyl chloride or dimethyl sulfate quaternary ammonium salt of 1-acryloyl-4-methyl piperazine and polymers thereof.

6 Claims, No Drawings

WATER-SOLUBLE QUATERNARY CATIONIC MONOMERS

The present application is a division of U.S. Ser. No. 621,339, filed June 15, 1984, now U.S. Pat. No. 4,659,828.

THE INVENTION

The present invention is concerned with the methyl chloride or dimethyl sulfate quaternary ammonium salts of 1-acryloyl-4-methyl piperaxine. It is also directed to the homopolymers as well as the acrylamide copolymers of these novel monomers.

The starting vinyl monomer used to prepare the ammonium salts is 1-acryloyl-4-methyl piperazine. This monomer is reacted with appropriate amounts of methyl chloride or dimethyl sulfate to produce the compounds of the invention. To prepare the starting materials, acryloyl chloride is reacted with N-methylpiperazine.

The monomers may be either homopolymerized or may be copolymerized with other vinyl addition monomers capable of being polymerized with the monomers of this invention. The resultant homopolymers will be water-soluble. Copolymers may be either water-soluble or water insoluble. A particularly useful water-soluble copolymer may be prepared by polymerizing the monomers of this invention with acrylamide. Homopolymers and copolymers of the monomers of this invention with acrylamide have a variety of industrial uses such as, for example flocculants and dewatering agents.

The monomers of this invention may be copolymerized with either water-soluble or water-insoluble vinyl addition monomers having suitable reactivity ratios. The co-monomers may be either nonionic, cationic, or anionic. Examples of suitable non-ionic monomers include: acrylamide, methacrylamide, acrylonitrile, vinyl acetate, lower alkyl acrylates, lower alkyl methacrylates, lower alkyl ethacrylates, styrene, etc. Examples of suitable anionic co-monomers useful in this invention include: acrylic acid, methacrylic acid, itaconic acid, maleic anhydride, acrylamidomethylpropanesulfonic acid, etc. Examples of suitable cationic monomers which may be useful in this invention include: dimethylaminoethylacrylate, quaternary salts of dimethylaminoethylacrylate, dimethylaminoethylmethacrylate, dimethylaminoethylmethacrylate quaternaries, diallyldimethylammonium chloride, methacrylamidopropyltrimethylammonium chloride, N-vinyl pyrrolidinone, vinyl pyridine, N,N-dimethylaminomethylacrylamide, N,N-dimethylaminomethylmethacrylamide, N,N-dimethylaminomethylacrylamide quaternaries, etc.

All that is important is that the co-monomer be capable of polymerizing, or have suitable reactivity ratios, with the monomers of this invention. Generally when copolymerized such copolymers will contain from 1–99 mole percent, preferably 1–70 mole percent and most preferably 2–50 mole percent of the comonomer or comonomers employed.

The polymers and copolymers of the invention can be prepared either using conventional solution polymerization techniques or the so-called inverse emulsion polymerization method which utilized polymerization of water-soluble vinyl monomers in the form of water-in-oil emulsions. This technique is described in Vanderhoff, U.S. Pat. No. 3,284,393, the disclosure of which is incorporated herein by reference.

EXAMPLES

To illustrate the invention, the following are given by way of example:

EXAMPLE 1

Synthesis of 1-acrylol-4-methyl piperazine

Acryloyl chloride (90.5 g) in methylene chloride (100 ml) was added into a methlene chloride (500 ml) solution of N-methyl piperazine (100 g) over a period of one hour. The reaction temperature was kept below 25° C. with cooling. After the addition was completed, the reaction mixture was stirred at ambient temperature for two hours. Then, sodium carbonate (53 g) in 250 ml of water was added into the reaction mixture with stirring. A crude product of (76 g) 1-acryloyl-4-methyl piperazine was recovered from the methylene chloride solution. The product was distilled and the fraction collected at 65°–69° C./1.5 mm Hg was characterized by I.R. and C13 NMR and was found to be 97% pure by GC.

EXAMPLE 2

Quaternization of 1-acryloyl-4-methyl piperazine

Dimethyl sulfate (45.8 g) was added slowly into 1-acryloyl-4-methyl piperazine (54.3 g) in water (99 g) with cooling so that the reaction temperature was kept below 30° C. After the addition was completed, the reaction mixture was stirred at ambient temperature for two hours. The product was characterized by C13 NMR.

Into a 300 ml Parr bomb was charged water (92.9 g), 1-acryloyl-4-methyl piperazine (70 g) and methyl chloride (27 g). The valves were closed and the bomb was heated to and maintained at 45° C. for 4 hours. C13 NMR of the product showed 90% of the starting amine was converted to quaternary salts.

EXAMPLE 3

This example illustrates a typical solution polymerization of the dimethyl sulfate quaternary ammonium salt of 1-acryloyl-4-methyl piperazine.

The following represented a charge to a polymerization reaction flask:

| | |
|---|---|
| 50% AMPIP MSQ[1] | 20 g. |
| H$_2$O | 70.8 g. |
| 2% ethylenediamine tetraacetic acid solution (Versene) | 1 ml. |

[1]AMPIP MSQ — 1-acryloyl-4-methyl piperazine dimethyl sulfate quaternary ammonium salt.

[1]AMPIP MSQ-1-acryloyl-4-methyl piperazine dimethyl sulfate quaternary ammonium salt.

The above charge was heated to 60° C. at which time 0.35 g. of ammonium persulfate in 5 ml. water was added to the contents of the flask. The reaction temperature was maintained at 60° C. for 3 hours at which point another 0.35 g. of ammonium persulfate solution was added. It was then heated for about 1 hour at 70° C. to complete the polymerization. The conversion was 91.4%. The intrinsic viscosity was 0.20. The Reduced Specific Viscosity at 0.045 g/100 cc. in 1MN$_a$NO$_3$, 30° C. was 0.20. The molecular weight was 1.8×10$^4$, and the Huggins Constant was 0.303.

EXAMPLE 4

As indicated, the above described monomers may be polymerized using the so-called "water-in-oil" emulsion technique. This method as used in the practice of this invention is generally described as follows:

The Water-in Oil Emulsions of the Methyl Chloride or DiMethyl Sulfate Quaternary Ammonium Salts of 1-Acryloyl-4-Methyl Piperazine The water-in-oil emulsions of the methyl chloride or dimethyl sulfate quaternary ammonium salts of 1-acryloyl-4-methyl piperazine (hereafter water-soluble vinyl addition polymers) in this invention contain four basic components. These components and their weight percentages in the emulsions are listed below:

A. Water soluble vinyl addition polymer:
1. Generally from 5–60%;
2. Preferably from 20–40%; and
3. Most preferably from 25–35%;

B. Water:
1. Generally from 20–90%;
2. Preferably from 20–70%; and
3. Most preferably from 35–55%;

C. Hydrophobic liquid:
1. Generally from 5–75%;
2. Preferably from 5–40%; and
3. Most preferably from 20–30%; and D. Water-in-Oil emulsifying agent:
1. Generally from 0.1–21%; 2. Preferably from 1–15%; and
3. Most preferably from 1.2–10%.

It is also possible to further characterize the water-in-oil emulsions of water-soluble vinyl addition polymers with respect to the aqueous phase of the emulsions. This aqueous phase is generally defined as the sum of the polymer or copolymer present in the emulsion plus the amount of water present in the emulsion. This terminology may also be utilized in describing the water-in-oil emulsions which are useful in this invention. Utilizing this terminology, the aqueous phase of the water-in-oil emulsions of this invention generally consists of 25–95% by weight of this emulsion. Preferably, the aqueous phase is between 60–90% and, most preferably, from 65–85% by weight of the emulsion.

The emulsions also may be characterized in relation to the water-in-oil ratios. This figure is simply a ratio of the amount of water present in the emulsion divided by the amount of hydrophobic liquid present in the emulsion. Generally, the water-in-oil emulsions of this invention will have a water-in-oil ratio of from 0.25 to 18. Preferably, the water-oil ratio will range from 0.5–14, and, most preferably, from 1.0–2.75.

EXAMPLE 5

| Oil Phase: | |
|---|---|
| LOPS | 130.0 g |
| Sorbitan Monooleate | 7.5 g |
| 4 moles EO reacted with Sorbitan Monostearate | 2.5 g |
| Aqueous Phase: | |
| 50% AMPIP MSQ | 51.25 g |
| 46.4% Acrylamide solution | 246.49 g |
| $H_2O$ | 59.92 g |
| Versene | .05 g |
| Initiator: | |
| 2,2'-Azobisisobutyronitrile | .28 g |

The oil phase and the aqueous phases with pH adjusted to 4.5 were first prepared and the emulsion was obtained by adding the aqueous solution into the LOPS solution with vigorous stirring.

The emulsion was purged with nitrogen for ½ hour and then heated to 45° C. The initiator was added and the reaction was maintained at 45° C. for four hours and at 65° C. for one hour. The reaction was stopped and cooled to room temperature. G.C. and L.C. analyses show the product contained only 350 ppm and less than 500 ppm of AMPIP MSQ and acrylamide respectively. The IV of the copolymer was 16.5 and the RS (@ 0.045 g/100 cc. in 1M $NaNO_3$) was 21.9.

Using the above polymerization techniques, a variety of homo and copolymers of the invention were prepared. The results of these syntheses are set forth below in Table I.

TABLE I

| COMP. NO. | COMPOSITION, M % CATIONIC | WT. % SOLIDS | RSV 0.045 g/ 100 c.c. in 1M $NaNO_3$ | IV |
|---|---|---|---|---|
| 1 | Latex AMPIP $MSQ^2$ AcAm, 1 | 28 | 27.7 | 18.3 |
| 2 | Latex AMPIP $MSQ^2$ AcAm, 5.4 | 28 | 25.3 | 23.5 |
| 3 | Latex AMPIP $MSQ^2$ AcAm, 5.4 | 28.1 | 21.9 | 16.5 |
| 4 | Latex AMPIP $MSQ^2$ AcAm, 5.4 | 28 | 12.7 | 10.0 |
| 5 | Latex AMPIP $MSQ^2$ AcAm, 8.7 | 24.1 | 9.9 | 7.9 |
| 6 | Solution AMPIP $MSQ^2$ AcAm, 9.0 | 4.6 | | 4.0 |
| 7 | Latex AMPIP $MSQ^2$ AcAm, 10.0 | 27.8 | 18.7 | 14.2 |
| 8 | Latex AMPIP $MSQ^2$ AcAm, 10.0 | 27.9 | 15.2 | 12.5 |
| 9 | Latex AMPIP $MSQ^2$ AcAm, 10.0 | 27.7 | 10.4 | 9.3 |
| 10 | Solution AMPIP $MSQ^2$ AcAm, 10.0 | 5.0 | 4.3 | 4.0 |
| 11 | Latex AMPIP $MSQ^2$ AcAm, 15.0 | 27.9 | 20.8 | 16.6 |
| 12 | Latex AMPIP $MSQ^2$ AcAm, 15.0 | 27.9 | 14.3 | 11.8 |
| 13 | Latex AMPIP $MSQ^2$ AcAm, 15.0 | 28.0 | 12.1 | 9.4 |
| 14 | Latex AMPIP $MSQ^2$ AcAm, 15.0 | 28.0 | 7.0 | 6.3 |
| 15 | Latex AMPIP $MSQ^2$ AcAm, 20.0 | 28.0 | 16.8 | 11.8 |
| 16 | Latex AMPIP $MSQ^2$ AcAm, 20.0 | 27.8 | 14.0 | 11.4 |
| 17 | Latex AMPIP $MSQ^2$ AcAm, 20.0 | 27.9 | 13.4 | 11.3 |
| 18 | Latex AMPIP $MSQ^2$ AcAm, 20.0 | 28.0 | 10.0 | 7.9 |
| 19 | Latex AMPIP $MSQ^2$ AcAm, 20.0 | 5.0 | 4.7 | 3.9 |
| 20 | Solution AMPIP MSQ AcAm, 22.9 | 33.5 | 0.06 | 0.06 |
| 21 | Solution AMPIP-AcAm, 22.5 | 27.8 | 0.11 | 0.11 |
| 22 | Solution AMPIP MSQ AcAm, 30 | 5.0 | 6.0 | 5.6 |
| 23 | Latex AMPIP MSQ AcAm, 31.5 | 25.5 | 8.8 | 7.1 |
| 24 | Latex AMPIP MSQ AcAm, 34.0 | 27.9 | 12.9 | 11.0 |

TABLE I-continued

| COMP. NO. | COMPOSITION, M % CATIONIC | WT. % SOLIDS | RSV 0.045 g/ 100 c.c. in 1M NaNO$_3$ | IV |
|---|---|---|---|---|
| 25 | Latex AMPIP MSQ AcAm, 34.0 | 28 | 12.9 | 10.2 |
| 26 | Latex AMPIP MSQ AcAm, 34.0 | 27.9 | 7.4 | 6.5 |
| 27 | Solution AMPIP MSQ AcAm, 37.8 | 4.1 | 1.9 | 1.8 |
| 28 | Latex AMPIP MSQ AcAm, 50 | 28.0 | 7.4 | 6.6 |
| 29 | Latex AMPIP MSQ AcAm, 50 | 27.9 | 7.3 | 6.1 |
| 30 | Latex AMPIP MSQ AcAm, 50 | 27.9 | 6.6 | 5.6 |
| 31 | Solution AMPIP MCQ[3] | 30 | 0.29 | 0.29 |
| 32 | Latex AMPIP MSQ | 32.6 | 2.76 | 2.62 |
| 33 | Solution AMPIP MSQ | 9.4 | | 2.6 |
| 34 | Solution AMPIP MSQ | 10.0 | | 1.8 |
| 35 | Solution AMPIP MSQ | 2.4 | 1.44 | 1.42 |
| 36 | Solution AMPIP MSQ | 10.0 | | 1.37 |
| 37 | Solution AMPIP MSQ | 9.5 | 1.07 | 1.07 |
| 38 | Solution AMPIP MSQ | 9.3 | | 0.77 |
| 39 | Solution AMPIP MSQ | 10.2 | | 0.23 |
| 40 | Solution AMPIP MSQ | 9.0 | 0.20 | 0.20 |
| 41 | Solution AMPIP MSQ | 17.0 | 0.03 | 0.03 |

[2]Dimethyl sulfate quaternary
[3]Methyl chloride quaternary

It is to be noted that when solution polymerizations are used, relatively low molecular weight polymers are formed, whereas then the water-in-oil emulsion technique is used, an increase in molecular weight is obtained.

Having thus described my invention, it is claimed:

1. The homopolymer of the dimethyl sulfate quaternary ammonium salt of 1-acryloyl-4-methyl piperazine.

2. The homopolymer of the methyl chloride quaternary ammonium salt of 1-acryloyl-4-methyl piperazine.

3. The copolymer of the dimethyl sulfate quaternary ammonium salt of 1-acryloyl-4-methyl piperazine with acrylamide, which copolymer contains between 1-99 mole percent of the dimethyl sulfate quaternary ammonium salt of 1-acryloyl-4-methyl piperazine.

4. The copolymer of the methyl chloride quaternary ammonium salt of 1-acryloyl-4-methyl piperazine with acrylamide, which copolymer contains between 1-99 mole percent of the methyl chloride quaternary ammonium salt of 1-acryloyl-4-methyl piperazine.

5. A copolymer of the dimethyl sulfate quaternary ammonium salt of 1-acryloyl-4-methyl piperazine, with a vinyl addition monomer.

6. A copolymer of the methyl chloride quaternary ammonium salt of 1-acryloyl-4-methyl piperazine, with a vinyl addition monomer.

* * * * *